US00PP13167P2

(12) United States Plant Patent
Mowrey et al.

(10) Patent No.: US PP13,167 P2
(45) Date of Patent: Nov. 5, 2002

(54) PLUM TREE NAMED 'SUPLUMTWENTYTHREE'

(75) Inventors: Bruce D. Mowrey, La Selva Beach; David W. Cain, Bakersfield, both of CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 09/793,065

(22) Filed: Feb. 26, 2001

(51) Int. Cl.[7] ..... A01H 5/00
(52) U.S. Cl. ..... Plt./184

(58) Field of Search ..... Plt./184

(56) References Cited

U.S. PATENT DOCUMENTS

PP10,285 P 3/1998 Zaiger et al. ..... Plt./38.1

*Primary Examiner*—Bruce R. Campell
*Assistant Examiner*—Susan B. McCormick
(74) *Attorney, Agent, or Firm*—Knobbe, Martens, Olson & Bear, LLP

(57) ABSTRACT

A new and distinct plum variety that possesses early ripening fruit which ripens evenly and has a mildly sweet taste is described. The fruit is not prone to fruit drop and has good keeping quality for the fresh market.

1 Drawing Sheet

LATIN NAME OF THE GENUS AND SPECIES OF THE PLANT CLAIMED

*Prunus salicina.*

VARIETY DENOMINATION

'Suplumtwentythree'.

BACKGROUND AND SUMMARY OF THE INVENTION

This invention relates to the discovery and asexual propagation of a new variety of plum, *Prunus salicina* cv. 'Suplumtwentythree'. The new variety was first hybridized by Bruce D. Mowery. The new variety 'Suplumtwentythree' was selected and evaluated by David W. Cain near Wasco, Kern County, Calif. The variety was originated by open pollination of an unnamed, unpatented Sun World international breeding plum selection, designated as 91P-001. The new variety is characterized by its early ripening fruit, which ripens evenly and has a mildly sweet taste. The fruit is not prone to fruit drop and has good keeping quality for the fresh market.

'Suplumtwentythree' has as its seed parent an unnamed, unpatented plum variety designated as 91P-001. The new plum variety cv. 'Suplumtwentythree' arose from an open pollination of the seed parent and thus the pollen parent is an unknown plum variety. The parent varieties were first crossed in 1993, with the date of sowing of November 1993 and first flowering being in 1996. The new 'Suplumtwentythree' variety was first asexually propagated by David W. Cain in May 1998, near Wasco, Kern County, Calif., by budding.

'Suplumtwentythree' differs from its seed parent, 91P-001, by producing fruits that are slightly larger than its parent, averaging 6.2 cm diameter while 91P-001 averages 5.5 cm diameter. Fruits of the new variety cv. 'Suplumtwentythree' have red-colored flesh, while the flesh of 91P-001 is yellow. Moreover, 'Suplumtwentythree' ripens approximately four days after its seed parent 91P-001. The new variety 'Suplumtwentythree' closely resembles its sibling 'Suplumtwentytwo,' but ripens approximately fourteen days after 'Suplumtwentytwo'.

'Suplumtwentythree' most nearly resembles the interspecific tree 'Flavorosa' variety (U.S. Plant Pat. No. 10,285). It is distinguished from the 'Flavorosa' variety by possessing more rounded elliptic leaves with less pronounced pointed lanceolate apices. The new variety is further differentiated from 'Flavorosa' by not being an interspecific hybrid with *Prunus armeniaca* parentage. 'Suplumtwentythree' fruits have flesh that tends to be lighter red near the pit cavity when commercially ripe as compared to the darker red coloration near the pit cavity in the 'Flavorosa variety'. Additionally, the fruits of the new variety are able to hold more tenaciously to the tree, resulting in fruit that is less prone to fruit drop as the fruit approach maturity, in contrast to the 'Flavorosa' variety. Fruits of the new variety ripen approximately fourteen days after 'Flavorosa'.

The flesh of 'Suplumtwentythree' fruit is red, in contrast to the yellow flesh of the 'Black Beaut' (U.S. Plant Pat. No. 3,617, expired) variety, and ripens approximately 5 days before 'Black Beaut'. The new plum variety cv. 'Suplumtwentythree' ripens approximately 14 days after the 'Red Beaut' (U.S. Plant Pat. No. 2,539, expired) variety.

The new plum variety cv. 'Suplumtwentythree' has been shown to maintain its distinguishing characteristics through successive asexual propagations by, for example, budding.

BRIEF DESCRIPTION OF THE FIGURE

The accompanying drawing in FIG. 1 illustrates in full color.

DETAILED BOTANICAL DESCRIPTION OF THE INVENTION

Figure 1:
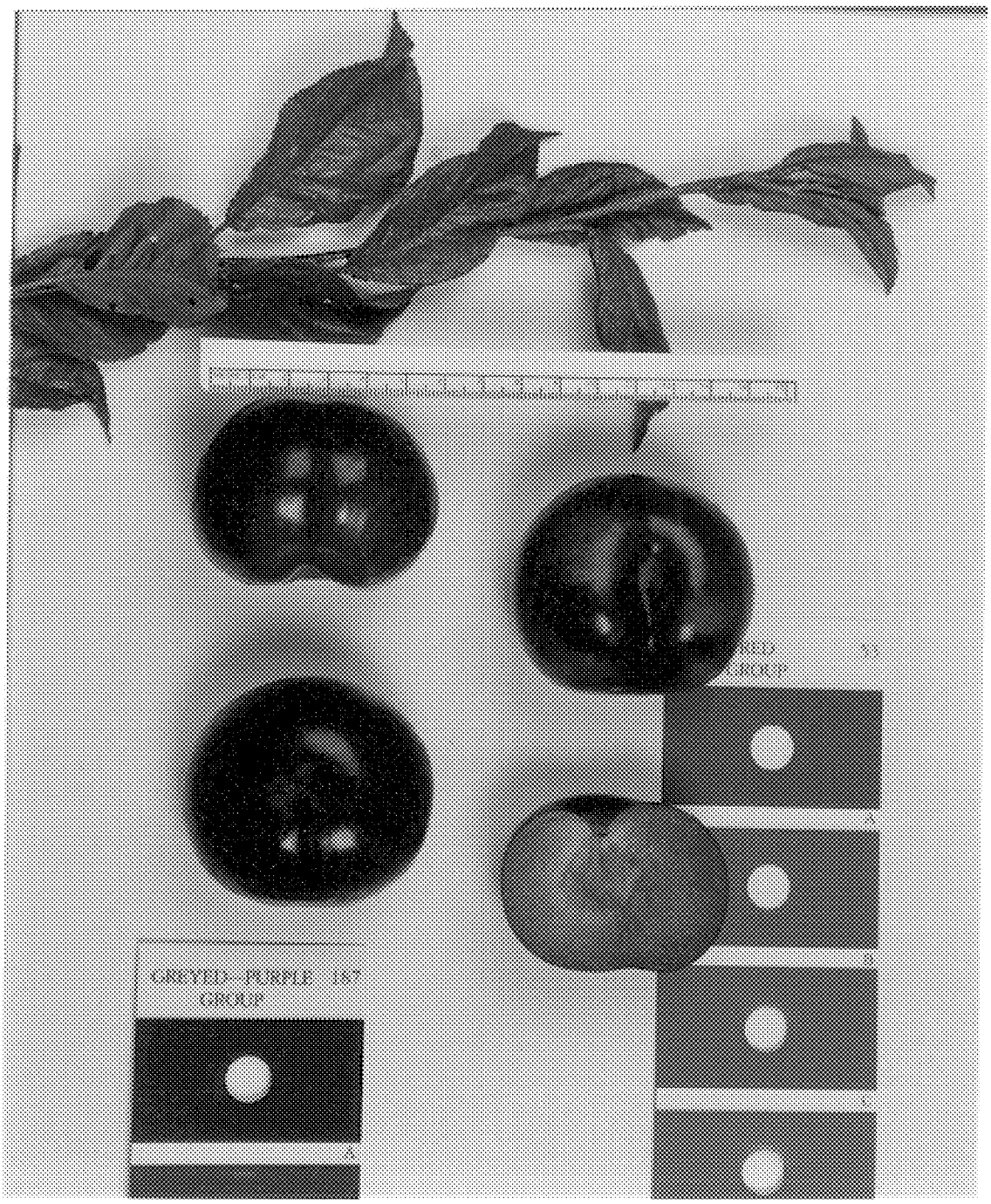

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 8 year old 'Suplumtwentythree' plants grown in the vicinity near Wasco, Kern County, Calif., during 2000, and is believed to apply to plants of the same variety grown under similar conditions of soil and climate elsewhere:

TREE

General:
- *Height of tree.*—Reduced by pruning to approximately 300 to 400 cm in height and maintained at about 250 cm wide.
- *Growth rate.*—About 45 to 100 cm in one year on a mature tree. Growth rate is affected by cultural and environmental factors.
- *Vigor.*—Medium.
- *Habit.*—Semi-upright.
- *Density of foliage.*—Medium.
- *Shape.*—Vase formed.
- *Hardiness.*—Hardy in Kern County, Calif.
- *Productivity.*—Productive.
- *Fruit bearing.*—Regular bearer.
- *Root stock.*—Flordaguard.

Trunk:
- *Diameter at 30 cm above soil level.*—About 20 cm.
- *Surface texture.*—Medium-shaggy.
- *Color.*—About 200 C.

Branches:
- *Shape.*—Round.
- *Diameter at 70 cm above soil line.*—Varies from about 7 to 9 cm (varies with age).
- *Surface texture.*—Smooth to medium shaggy.
- *Color.*—About 166B to 200C.
- *Surface appearance.*—Semi-glossy.

Lenticels:
- *Number.*—Few.
- *Size.*—About 0.8 mm in diameter.
- *Color.*—About 156B.

LEAVES

General:
- *Average length.*—About 10.2 cm.
- *Average width.*—About 4.4 cm.
- *Size.*—Large-medium.
- *Outline.*—Broad obovate to elliptical.
- *Profile.*—Up folded.
- *Leaf blade tip.*—Curved downwardly.
- *Angle of tip.*—Acute to right angle.
- *Margin.*—Crenate.
- *Undulation of margin.*—Medium.
- *Apex.*—Cuspidate.
- *Base.*—Cuneate.
- *Thickness.*—Medium.
- *Venation pattern.*—Pinnate.
- *Vein color.*—144C.

Upper surface:
- *Color.*—About 147A.
- *Glossiness.*—Weak.
- *Pubescense.*—Absent.
- *Surface texture.*—Smooth.
- *Surface appearance.*—Dull.

Lower surface:
- *Color.*—About 147B.
- *Glossiness.*—Weak.
- *Pubescense.*—Absent.
- *Surface texture.*—Smooth.
- *Surface appearance.*—Dull.

Petiole:
- *Length.*—Medium, about 1 cm.
- *Thickness.*—Medium, about 2 mm.
- *Color.*—About 144A, with highlights of red 47B.

Glands:
- *Average number.*—3.
- *Positioning.*—(A) On both leaf base and petiole; (B) Alternate.
- *Size.*—About 0.8 mm long by 0.8 mm wide.
- *Shape.*—Globose.
- *Color.*—About 147A, becoming about Red-Purple 59A as it ages.

Stipules:
- *Persistence.*—Persistent.

Wood (leaf) buds:
- *Shape.*—Conical.
- *Width of bud (on 5 mm diameter flowering shoot).*—About 2 mm wide (at widest point).
- *Length (on 5 mm diameter flowering shoot).*—About 2.5 mm long.
- *Position relative to shoot.*—Held out.
- *Support.*—Not decurrent.
- *Time of bud burst.*—Occurs at about the first bloom date.

Flowering shoots:
- *Anthocyanin coloration.*—Present.
- *Intensity.*—Medium.
- *Thickness.*—Medium, about 0.47 cm.
- *Internode length.*—Medium, about 1.9 cm.
- *Density of buds.*—Medium.
- *Distribution.*—Isolated in groups of 2 or more on spurs and one year old shoots and older wood.
- *Ratio of wood (leaf) buds to flowering shoots.*—1:4 (ranges from 1:4 to 1:6).

FLOWERS

Flower-buds:
- *Hardiness.*—Hardy.
- *Size.*—About 3 mm wide at widest point, by about 3.5 mm in length.
- *Length.*—Medium.
- *Shape.*—Ovoid.
- *Positioning.*—Free.
- *Pubescence.*—Absent.
- *Color.*—About 177A.

General:
- *Date of first bloom.*—Mar. 3, 2000.
- *Date of full bloom.*—Mar. 8, 2000.
- *Time of bloom.*—Medium, as compared with similar varieties in the growing area of Wasco, Kern County, Calif.
- *Duration of bloom.*—Medium, about 10 days.
- *Size (diameter of the fully open flower).*—Medium, about 2.1 cm.
- *Shape.*—Rosaceous.
- *Petals.*—Free.
- *Color (fully opened flower).*—White.

Peduncle:
- *Length.*—Medium, about 0.7 cm.
- *Diameter.*—0.9 mm.

*Color.*—About 145A.
*Pubescence.*—Absent.
Receptacle:
*Depth.*—Medium.
*Pubescence of inner surface* (*at white bud stage*).—Absent.
*Pubescence of outer surface.*—Absent.
Sepals:
*Length.*—About 2.5 mm.
*Width.*—About 2.0 mm at widest point.
*Color.*—About 145A.
*Positioning.*—Adpressed to petals.
*Shape.*—Ovate.
*Pubescence of inner surface.*—Absent.
*Pubescence of outer surface.*—Absent.
*Frequency of flowers with double sepals.*—None.
Petals:
*Frequency of flowers with double petals.*—None.
*Size.*—Medium.
*Width.*—About 0.8 cm.
*Length.*—About 1 cm.
*Shape.*—Transverse broad elliptic.
*Apex shape.*—Rounded.
*Base shape.*—Petal narrows as it nears base.
*Claw length.*—Short.
*Margin waviness.*—Medium.
*Base angle.*—Medium.
*Division of upper margin.*—Entire.
*Pubescence of inner surface.*—Absent.
*Pubescence of outer surface.*—Absent.
*Color* (*inner surface*).—White.
*Color* (*outer surface*).—White.
Stigma:
*Position* (*as compared with anthers*).—Level.
Anthers:
*Color* (*just before dehiscence*).—About Yellow 23B with slight shadings of about Red 45D.
Pollen:
*Color.*—About 13A.
Stamens:
*Position.*—Perigynous.
Pistil:
*Length at full bloom.*—About 7 mm.
*Frequency of supplementary pistils.*—Absent.
*Number.*—Always one.
Ovary:
*Pubescence.*—Absent.
*Diameter.*—About 0.9 mm.
*Color.*—About 143A.
Style:
*Shape.*—Slender.
*Color.*—About 145B.
*Pubescence* (*of base*).—Absent.

FRUIT

General:
*Maturity when described.*—Firm — ripe.
*Date.*—Jun. 3, 2000.
*Size.*—Uniform; medium-large; about 112 g.
*Length from stem end to apex.*—About 4.7 cm.
*Diameter in line with suture plane.*—About 5.9 cm.
*Diameter perpendicular to suture plane.*—About 6.2 cm.
*Form.*—Oblate-rounded.
*Position of maximum diameter.*—Towards middle.
*Symmetry about the suture.*—Nearly symmetric.
*Season ripening.*—Early.
*Use.*—Fresh market.
*Keeping quality.*—Good.
*Resistance to.*—Insects: medium; typical of Japanese type plums. Diseases: medium; typical of Japanese type plums. Shipping quality: good. Fruit stored for 3 weeks at 38° F.–42° F. showed no internal browning or mealiness of flesh.
Suture: An inconspicuous line, the suture is shallow and extends from base to apex.
Ventral surface:
*Shape.*—Rounded slightly.
*Lips.*—Equal.
*Depression of apex.*—Slightly-depressed.
*Pistil base.*—Not persisting.
*Pubescence at apex.*—Absent.
Stem cavity:
*Shape.*—Rounded and slightly elongated in suture plane sides.
*Depth.*—About 0.8 cm.
*Breadth.*—About 1.1 cm.
*Markings.*—None.
Base:
*Shape.*—Rounded-truncate.
Apex:
*Shape.*—Truncate and slightly depressed.
Pistil point:
*Shape.*—Slightly depressed.
Stem:
*Length.*—Medium, about 1.5 cm.
*Color.*—About 143C.
*Adherence to stone.*—Stem adheres to stone moderately but separates from the stone more readily than from the tree.
Skin:
*Thickness.*—Medium.
*Texture at harvest.*—Smooth and crisp.
*Reticulation.*—Absent.
*Roughness.*—Absent.
*Taste.*—Slightly tart.
*Tenacity.*—Tenacious to flesh.
*Tendency to crack.*—None in wet-dry season.
*Color.*—About 187A, becoming black as it ripens.
*Down* (*pubescence*).—None.
*Bloom.*—Present.
Flesh:
*Color.*—About Red 53A; lighter colored near the stone (about 48C) if not fully mature.
*Surface of the pit cavity.*—Slightly rough.
*Amygdalin.*—Wanting.
*Juice.*—Abundant to moderate.
*Sugar content.*—Medium (about 15% SS).
*Texture.*—Medium, fine, melting.
*Fibers.*—Medium, fine, tender.
*Ripens.*—Even.
*Flavor.*—Mildly sweet.
*Aroma.*—Distinct.
*Eating quality.*—Good.
*Stone/flesh ratio.*—1.7 g/115 g.

STONE

General:
*Adherence to flesh.*—Cling.
*Fibres.*—Retains short fibre.
*Size.*—Medium.
*Length.*—About 2 cm.

*Breadth.*—About 1.9 cm.
*Width of stalk end.*—About 0.2 cm.
*Angle of stalk end.*—Right angle to obtuse.
*Thickness.*—About 1.2 cm.
*Form* (*profile*).—Globose-elliptical.
*Form* (*ventral view*).—Sub-globular.
*Base.*—Nearly straight.
*Hilum.*—Narrow.
*Apex.*—Obtuse with a small sharp point.
*Position of maximum breadth.*—Middle, but varies with the growth of the keel.
*Sides.*—Nearly equal.
*Surface.*—Irregularly furrowed near base, rough but not heavily pitted.
*Outgrowing keel.*—Well developed.
*Ridges.*—Jagged.
*Pits.*—Angular.
*Ventrical edge.*—Thin with wing throughout.
*Dorsal edge.*—Medium width with distinct shallow groove throughout.
*Color of stone.*—About 164B.
*Tendency to split.*—Slight in wet/dry season.
*Kernel length when dried.*—About 12.2 mm.
*Kernel diameter in line with suture plane.*—About 10.1 mm.
*Kernel diameter perpendicular to suture plane.*—About 5 mm.
*Kernel astringency.*—Bitter.
*Kernel shape.*—Oval.
*Kernel viability.*—Viable.

What is claimed is:

1. A new and distinct plum tree as herein described and illustrated.

* * * * *